(12) United States Patent
Takizawa et al.

(10) Patent No.: US 7,511,733 B2
(45) Date of Patent: Mar. 31, 2009

(54) CAPSULE-TYPE MEDICAL APPARATUS

(75) Inventors: Hironobu Takizawa, Hachioji (JP);
Hideyuki Adachi, Sagamihara (JP);
Hitoshi Mizuno, Koganei (JP); Hisao Yabe, Hachioji (JP); Hiroki Moriyama, Akishima (JP)

(73) Assignee: Olympus Corporation, Tokyo (JP)

( * ) Notice: Subject to any disclaimer, the term of this patent is extended or adjusted under 35 U.S.C. 154(b) by 301 days.

(21) Appl. No.: 10/205,530

(22) Filed: Jul. 25, 2002

(65) Prior Publication Data
US 2003/0020810 A1   Jan. 30, 2003

(30) Foreign Application Priority Data
Jul. 30, 2001   (JP) .............................. 2001-229951

(51) Int. Cl.
*H04N 7/18* (2006.01)
(52) U.S. Cl. .............................. 348/68; 348/65; 348/77; 348/73; 600/114; 600/109; 600/160; 600/112; 600/129; 600/121; 600/101
(58) Field of Classification Search .................. 348/68, 348/65, 77, 76, 72, 64, 73; 455/100; 600/101, 600/109, 114, 160, 112, 122, 133, 585, 129, 600/121
See application file for complete search history.

(56) References Cited

U.S. PATENT DOCUMENTS

| | | | | |
|---|---|---|---|---|
| 5,604,531 A | * | 2/1997 | Iddan et al. .................. 348/76 |
| 5,653,677 A | * | 8/1997 | Okada et al. ................. 600/112 |
| 5,681,260 A | * | 10/1997 | Ueda et al. .................. 600/114 |
| 5,860,914 A | * | 1/1999 | Chiba et al. ................. 600/151 |
| 5,989,230 A | * | 11/1999 | Frassica ...................... 604/264 |
| 6,210,322 B1 | * | 4/2001 | Byrne ......................... 600/158 |
| 6,251,085 B1 | * | 6/2001 | Tezuka ........................ 600/585 |
| 6,632,175 B1 | * | 10/2003 | Marshall ..................... 600/309 |

FOREIGN PATENT DOCUMENTS

| | | | |
|---|---|---|---|
| JP | 57-45833 | | 3/1982 |
| JP | 2000296102 A | * | 10/2000 |
| JP | 2001-95755 | | 4/2001 |

* cited by examiner

*Primary Examiner*—Shawn An
(74) *Attorney, Agent, or Firm*—Scully, Scott, Murphy & Presser, P.C.

(57) ABSTRACT

A battery self-containing body, which self-contains a battery or a battery accommodating body, which accommodates a battery removably is attached to a capsule body including a drive circuit for driving an imaging device and an illuminating device. Thus, the power supply can be turned ON easily. In addition, the inside portion is sealed water-tightly. Thus, the battery self-containing body or a battery can be exchanged easily, which allows the easy reuse. The direction of the visual field of the imaging device is diagonal with respect to the axis of the capsule body. Furthermore, spiral-shape projections are provided on the peripheral surface of the cylinder form. Thus, the rotation allows the surface of canal cavity wall to be examined easily.

17 Claims, 14 Drawing Sheets

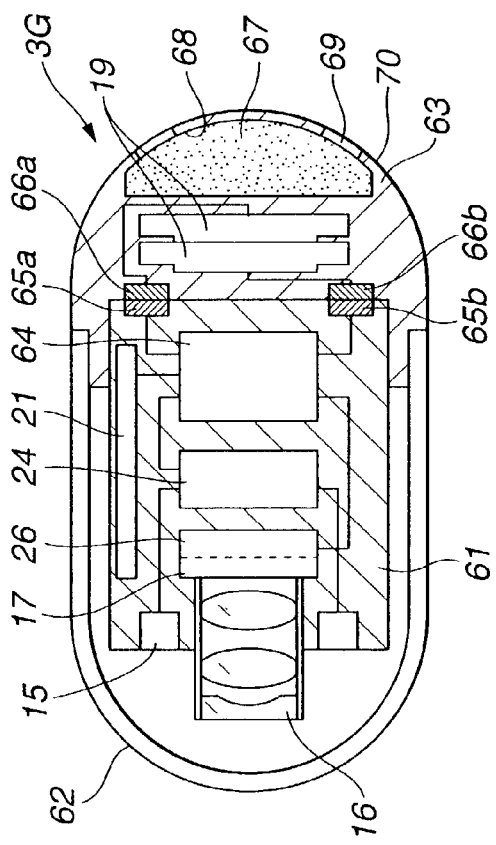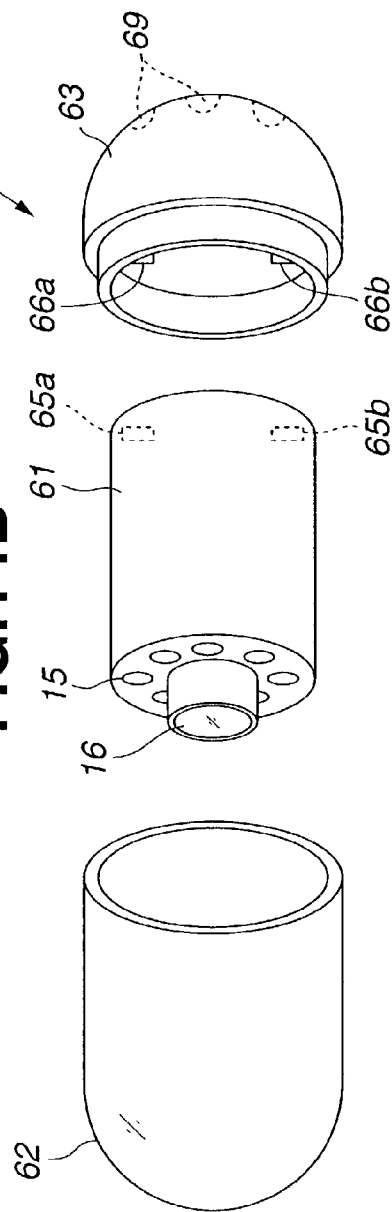
FIG.14A
FIG.14B

CAPSULE-TYPE MEDICAL APPARATUS

This application claims benefit of Japanese Application No. 2001-229951 filed on Jul. 30, 2001, the contents of which are incorporated by this reference.

BACKGROUND OF THE INVENTION

1. Field of the Invention

The present invention relates to a capsule-type medical apparatus for examining the inside of a body cavity, for example.

2. Description of the Related Art

Recently, an endoscope for observing and/or diagnosing the inside of a body cavity by inserting a long and narrow inserting portion has been widely used.

On the other hand, a capsule endoscope for observing the depths within a body cavity is disclosed in Japanese Patent Application 2001-95755, for example. The disclosed capsule endoscope is in form of capsule to be swallowed by a patient, which alleviates pain felt by the patient.

According to the capsule endoscope of the related art, a battery provided within a capsule container is used as a power supply to illuminate a subject by using an illuminator. Then, an image of the subject is focused on an image sensor by using an objective lens. An image signal from the image sensor is sent to the outside of the body by radio waves.

Also, U.S. Pat. No. 5,604,531 discloses a similar capsule endoscope. The disclosed capsule endoscope accommodates a battery within a capsule container, which is used as a power supply to send a signal imaged by using a CCD camera to the outside of a body.

In these technologies of the related art, the battery, which is associated with, for example, a CCD driver for driving a CCD camera, is accommodated within the capsule container. Thus, when the capsule endoscope is reused after it is swallowed by the patient once for the internal examination, the electric energy in the battery may be consumed. As a result, it is difficult to reuse.

SUMMARY OF THE INVENTION

Accordingly, it is an object of the present invention to provide a capsule-type medical apparatus, which is easy to reuse by replacing a battery or a battery peripheral portion.

It is another object of the present invention to provide a capsule-type medical apparatus, which allows the easy power-supply switching.

It is another object of the present invention to provide a capsule-type endoscope, which can improve the observation functionality by the revolution thereof in a body cavity.

Accordingly, there is provided a capsule-type medical apparatus, including a capsule body portion having an imaging device for imaging and an illuminating device for illumination, a power-supply portion, which is separate from the capsule body portion and self-contains a battery, and a removable mechanism having a water-tight internal portion, which is achieved by attaching the power-supply portion to the capsule body portion. Thus, the capsule-type medical apparatus can be reused easily by replacing the battery or the power-supply portion.

BRIEF DESCRIPTION OF THE DRAWINGS

FIGS. 1 to 7 relate to a first embodiment of the present invention;

FIG. 1 is an entire view of a capsule endoscope system including the first embodiment;

FIG. 2 is an external view of a capsule endoscope according to the first embodiment;

FIG. 3 is a diagram-showing an internal configuration of the capsule endoscope;

FIG. 6 is a diagram showing an internal configuration of a capsule endoscope in a variation example;

FIG. 7 is an explanatory diagram of an operation of the capsule-endoscope in FIG. 6;

FIGS. 8A to 13 relate to a second embodiment of the present invention;

FIGS. 8A and 8B are a front view and a perspective view showing an appearance of a capsule endoscope according to the second embodiment;

FIG. 10 is an explanatory diagram of another operation of this embodiment;

FIG. 11 is a diagram showing a capsule endoscope in a variation example;

FIG. 13 is a diagram showing a capsule endoscope in another variation example;

FIGS. 14A to 21 relate to a third embodiment of the present invention;

FIG. 14A is a diagram showing an internal construction of a capsule endoscope according to the third embodiment;

FIG. 14B is an exploded, perspective diagram showing the capsule endoscope of the third embodiment;

FIG. 15 an exploded, perspective view of a capsule endoscope in a first variation example;

FIG. 16 is an exploded, perspective diagram of a part of a capsule endoscope in a second variation example;

FIG. 18 is a sectional diagram showing a construction of a capsule endoscope in a fourth variation example;

FIG. 19 is a diagram showing a configuration of a magnetic field generating device in use;

FIG. 20 is a partially cut-out, sectional diagram of a capsule endoscope in a fifth variation example; and FIG. 21 is an explanatory diagram showing an observation visual field when the capsule endoscope is revolved.

DETAILED DESCRIPTION OF THE PREFERRED EMBODIMENTS

Embodiments of the present invention will be described below with reference to drawings.

First Embodiment

A first embodiment of the present invention will be described with reference to FIGS. 1 to 7.

Figure 1:
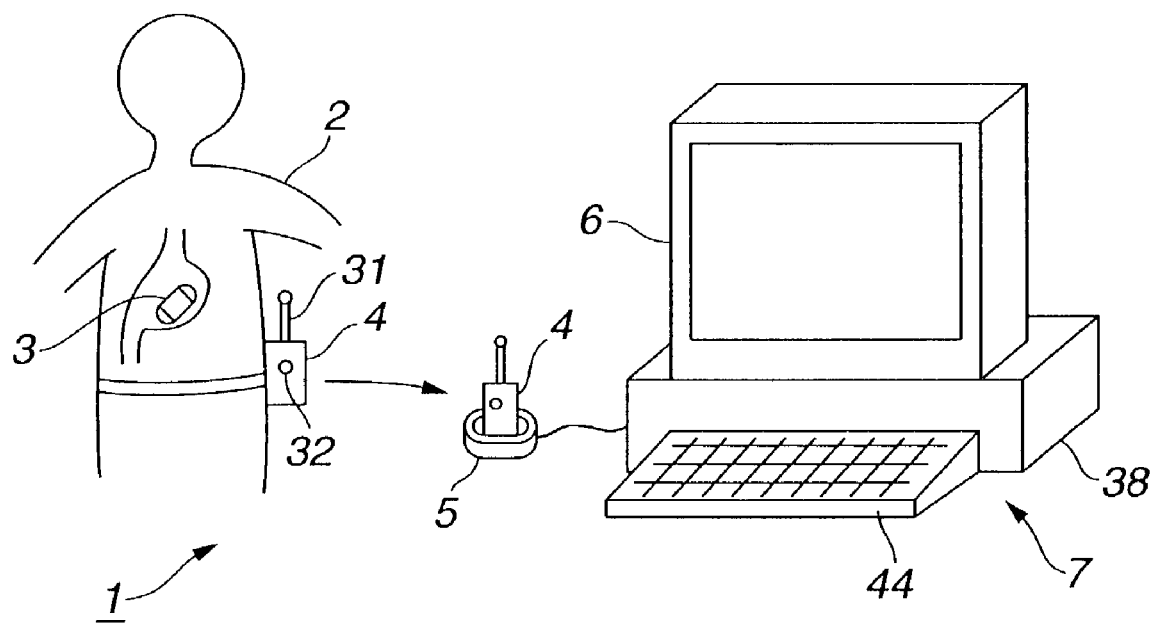

As shown in FIG. 1, a capsule endoscope system 1 includes a capsule endoscope 3 for examining the inside of a body of a patient 2, an external unit 4 for receiving image data from the capsule endoscope 3 and for storing the image data, an external unit attaching portion 5, which allows the external unit 4 to be attached removably, and a display system 7 for reading signal data stored in the external unit 4 and for displaying it in a display device 6.

Figure 2:
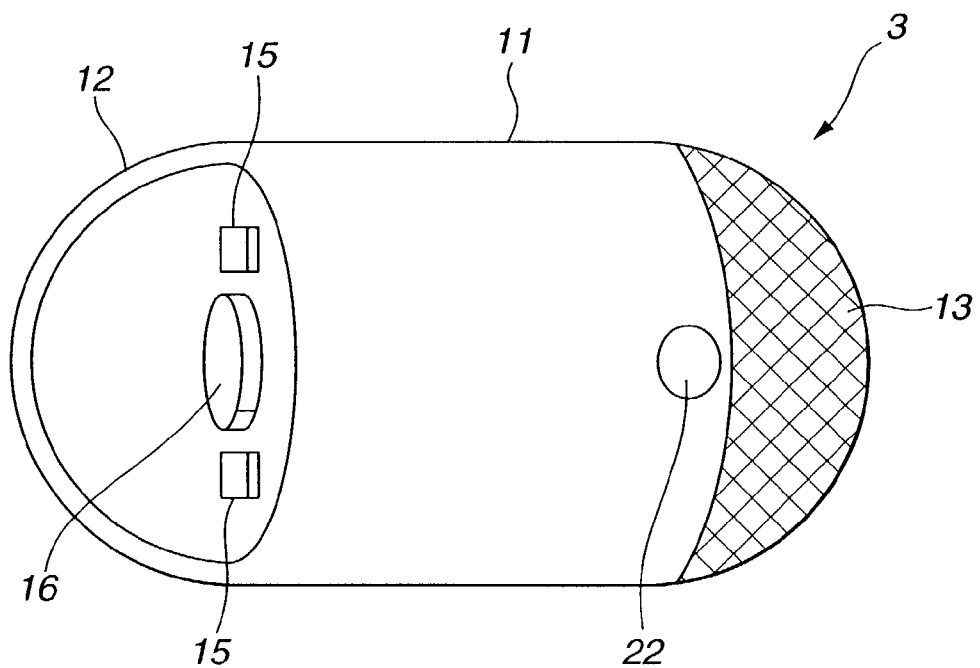
Figure 3:
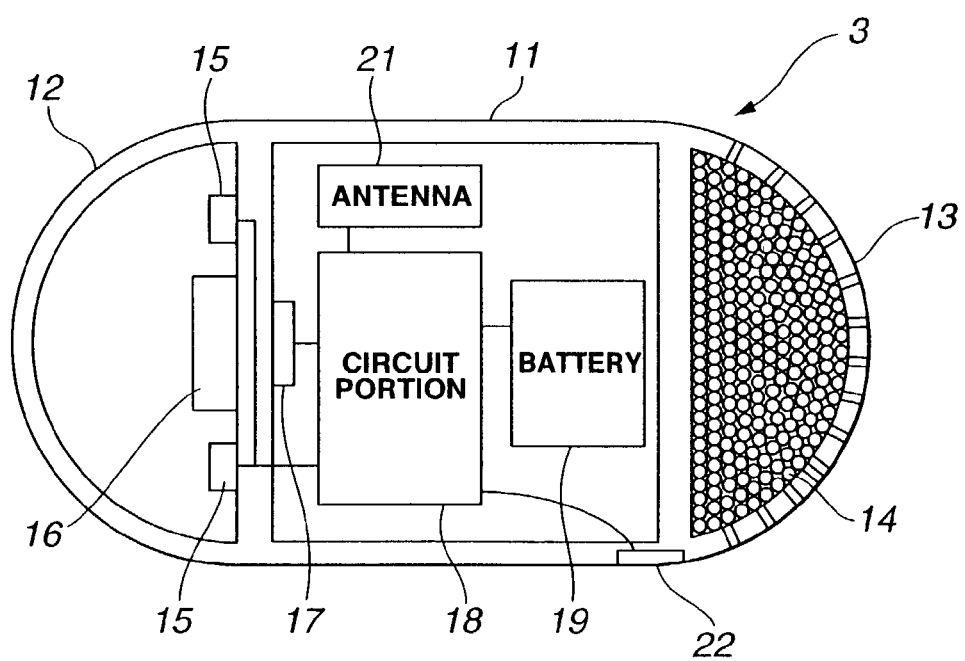

As shown in FIGS. 2 and 3, the capsule endoscope 3 is in a capsule form, which is a cylinder having both ends in a hemisphere form.

More specifically, as shown in FIG. 3, the capsule endoscope 3 has a capsule frame body 11, which is in a cylinder form having both ends being closed. One of the end surfaces of the capsule frame body 11 is in a domical form covered with a hemisphere transparent member 12 and accommodates an illumination and observation optical system inside. The other end surface is covered with a hemisphere mesh member 13, and microcapsules 14 containing a forming agent are filled inside. The forming agent contains sodium carbonate and organic acid.

Each of the microcapsules 14 in which the forming agent is filled is, for example, in a sphere form. The diameter is set larger than the size of the mesh portion of the mesh member 13. Thus, the microcapsules 14 do not spill to the outside of the mesh member 13. The microcapsules 14 are also arranged to expose the internal forming agent when ultrasonic waves, for example, are irradiated to the microcapsules 14 so as to destroy the microcapsules 14. The forming agent vaporizes when it reacts on water. Then, a large amount of gas is generated so that the forming agent can exhibit its function fully.

The objective lens 16 included in an imaging optical system is mounted at the center of one of end surfaces, which is the observing side, of the capsule frame body 11 within the end covered by the domical-form transparent member 12. LED's 15 are mounted as an illuminating optical system at multiple positions, for example, at four positions around the objective lens 16. Thus, the visual field range of the objective lens 16 can be illuminated.

A CMOS imager 17, for example, is mounted on the capsule frame body 11 at a position imaged by the objective lens 16.

The capsule frame body 11A self-contains a circuit portion 18 for performing signal processing and the like on the CMOS imager 17, a battery 19 for supplying power to operate the circuit portion 18 and an antenna 21 for sending image data imaged by the CMOS imager 17 to the external unit 4 by radio waves.

A pH sensor 22 for detecting whether or not the capsule endoscope 3 reaches a part to be examined, that is, the degree of acid (pH), is mounted such that it can be exposed on the external surface of the capsule endoscope 3. A detection signal from the pH sensor 22 is input to the circuit portion 18.

Based on the pH detected by the pH sensor 22, a fact that the capsule endoscope 3 reaches a part to be examined within the body is detected. According to this embodiment, a fact that the capsule endoscope 3 reaches the colon, for example, is detected. When the fact that the capsule endoscope 3 reaches the colon is detected, the detected signal is sent to the outside of the body.

Figure 4A:
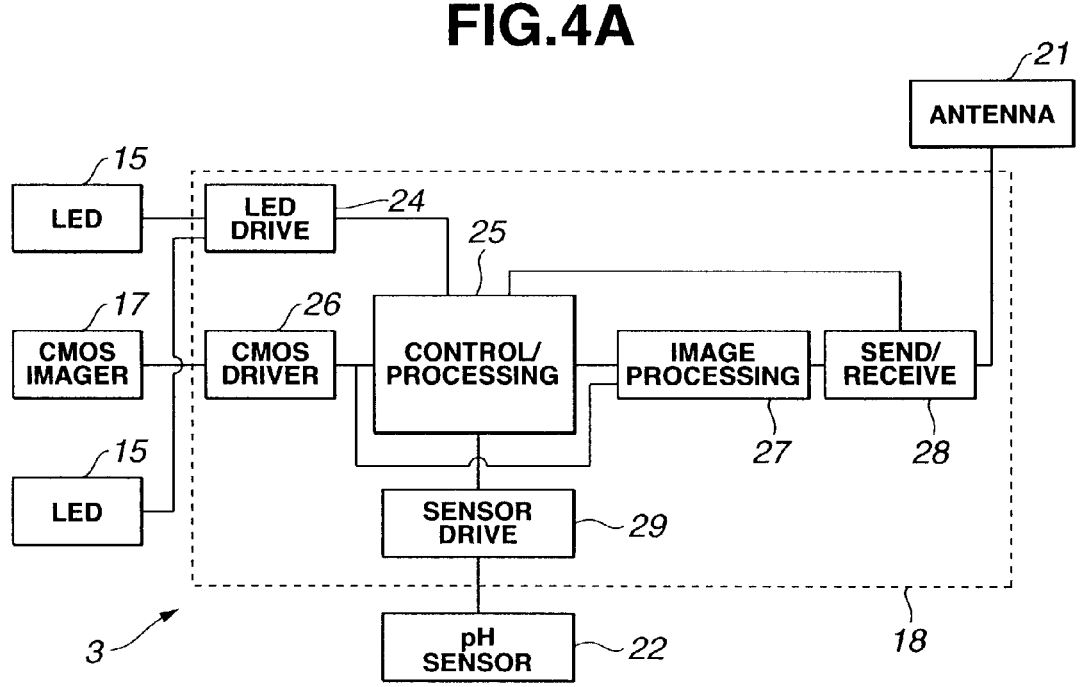
FIG. 4A is a block diagram showing an electric configuration of the capsule endoscope.

FIG. 4A shows a configuration of an electric system of the capsule endoscope 3 in more detail. Each of the LED's 15 is driven by an LED drive circuit 24. The LED's 15 emit white light so as to illuminate inside of the body.

The LED drive circuit 24 is controlled by a control signal from a control/processing circuit 25.

A subject within the body, which is illuminated by the LED's 15, is imaged by the objective lens 16 on the CMOS imager 17, and is optoelectronic-converted by the CMOS imager 17.

The signal, which is optoelectronic-converted by the CMOS imager 17, is read out by a drive signal from a CMOS driver 26. Then, the read signal is input to an image processing circuit 27 through the CMOS driver 26. Operations of the CMOS driver 26 and the image processing circuit 27 are also controlled by the control/processing circuit 25.

Then, the signal is converted to a compressed image signal by the image processing circuit 27 and is modulated with a high-frequency (for example, 2.4 GHz) through a send/receive circuit 28. Then, the signal is sent from an antenna 21 to the external unit 4 side in the outside of the body. The pH sensor 22 is driven by the sensor drive circuit 29, and the detection signal is input to the control/processing circuit 25 through the sensor drive circuit 29.

When the control/processing circuit 25 detects a predetermined pH, the fact is sent to the outside of the body through the send/receive circuit 28.

On the other hand, the external unit 4 for receiving image data and the like from the capsule endoscope 3 is in a box or cylinder form, having an antenna 31, for example. The external unit 4 is attached to the abdominal region of the patient 2 by using a belt, for example, as shown in FIG. 1.

Figure 4B:
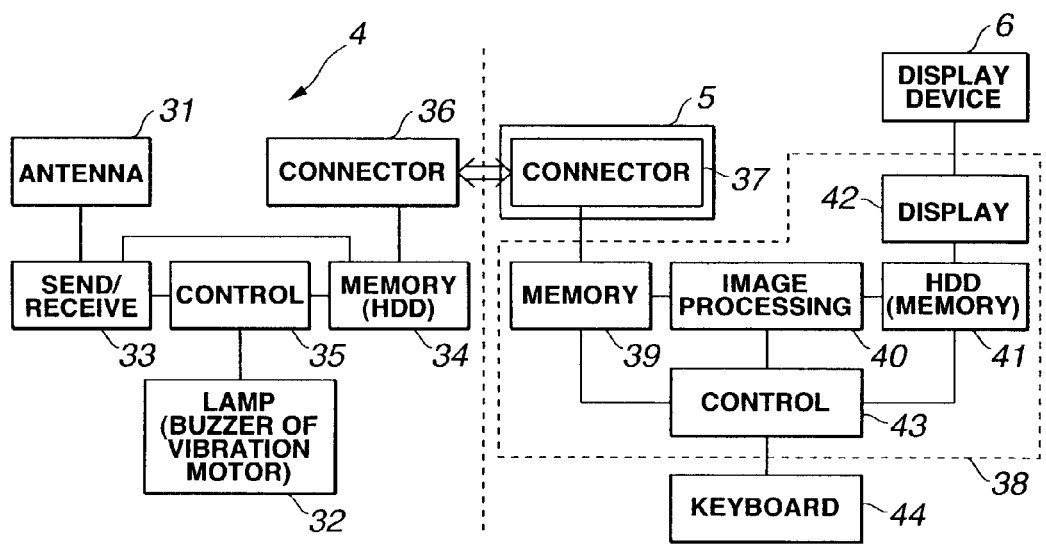
FIG. 4B is a block diagram showing electric configurations of an external unit and a display system.

When the external unit 4 receives a signal indicating the detection of the predetermined pH from the capsule endoscope 3, a lamp 32 is turned on and off (instead of turning the lamp 32 on and off as shown in FIG. 4B, the notification may be given by buzzing or vibration caused by a vibration motor).

A configuration of an electric system in the external unit 4 is shown in FIG. 4B.

The signal received by the antenna 31 is demodulated by the send/receive circuit 33. The demodulated image data is stored in a memory 34 (instead of the memory 34, a hard disk may be used, which is abbreviated by HDD in FIG. 4B and so forth. The send/receive circuit 33 and the memory 34 are controlled by a control circuit 35.

When a signal indicating the predetermined pH detected by the pH sensor 22 is detected in the demodulation processing by the send/receive circuit 33, the detection signal is sent to the control circuit 35. Then, the control circuit 35 turns the lamp 32 on and off.

Figure 5A:
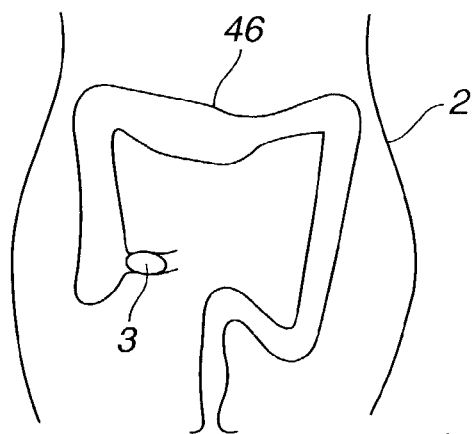
FIGS. 5A to 5D are explanatory diagrams for an operation of this embodiment.
Figure 5B:
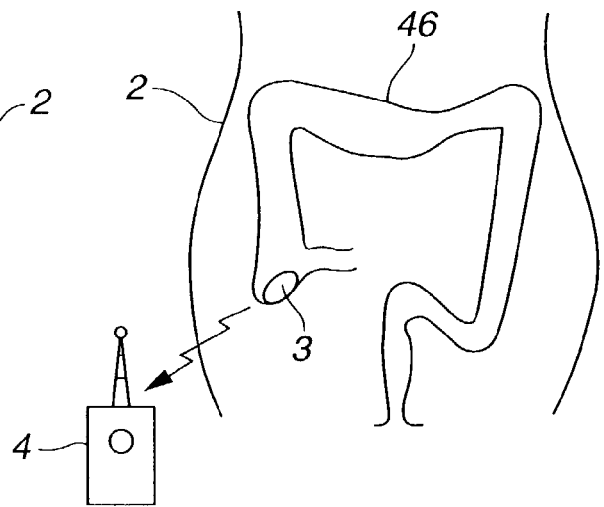
Figure 5D:
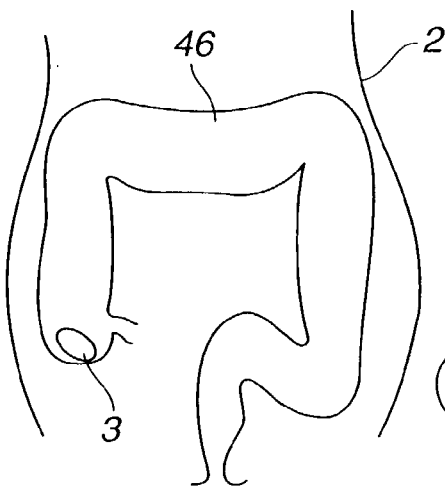
Figure 5C:
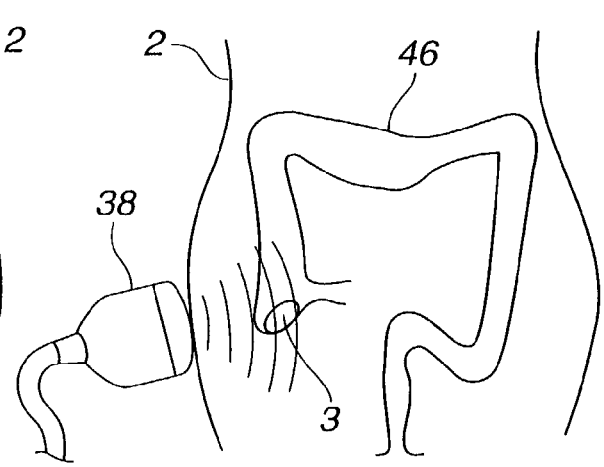

As described later, turning the lamp 32 on and off means that the capsule endoscope 3 reaches the part to be endoscope-examined. As shown in FIG. 5C, the user destroys the microcapsules 14 by pressing an external ultrasonic wave generator 38, for example, onto the abdominal region of the patient 2 in order to generate ultrasonic waves. Thus, the forming agent within the microcapsules 14 can be discharged to the outside of the microcapsules 14.

The forming agent reacts on water within the colon, and the forming agent is vaporized so as to expand the inside of the colon. When the control circuit 35 turns the lamp 32 on and off, for example, or after a short period of time since then, a control operation is performed for sending a control signal, which causes the capsule endoscope 3 side to start imaging, from the antenna 31 through the send/receive circuit 33.

The capsule endoscope 3 receives the control signal by using the antenna 21. Then, the control signal is demodulated by the send/receive circuit 28 and is sent to the control/processing circuit 25. When the control/processing circuit 25 identifies that the control signal is for starting imaging (by comparing or by referring to data pre-stored in the internal memory, for example), the control/processing circuit 25 operates the LED drive circuit 24, the CMOS driver 26, the image processing circuit 27 and the send/receive circuit 28 intermittently, for example.

For example, the LED's 15 emit light once per second for 1/30 of a second. After 1/30 of a second, the CMOS driver 26 applies a drive signal to the CMOS imager 17 and reads out imaged signals. The signals are image-processed and converted to compressed image signals in the image processing circuit 27. Then, the signals are high-frequency modulated through the send/receive circuit 28 and are sent from the antenna 21.

After sending a control signal, the control circuit 35 performs a control operation by converting the demodulated image signals received by the antenna 31 to digital image data and by writing the digital image data in the memory 34.

The memory 34 is connected to a connector 36. The image data stored in the memory 34 can be output through the connector 36.

The connector 36 can be attached removably to a connector 37 of the external unit attaching portion 5. After the connector 36 is attached, the image data in the memory 34 can be transferred to a personal computer body 38 side including in the display system 7.

The personal computer body 38 has a memory 39, an image processing circuit 40, a hard disk (or memory) 41, a display circuit 42, and a control circuit 43. The memory 39 is connected to a connector 37, for example, and functions as a buffer for temporally storing image data. The image processing circuit 40 is connected to the memory 39 for performing processing for expanding image data, for example. The hard disk 41 is connected to the image processing circuit 40 for storing the expanded image. The display circuit 42 is connected to the hard disk 41 for converting the stored image data to signals for display. The control circuit 43 controls the memory 39, the image processing circuit 40 and the hard disk 41. The image in the display circuit 42 is displayed by the display device 6.

The control circuit 43 is connected to a console such as a keyboard 44. When an instruction for image display, for example, is input from the key board 44 to the control circuit 43, the control circuit 43 performs the instructed processing such as image display, for example.

An operation will be described when the colon, for example, is endoscope-examined by using the capsule endoscope system 1 in this configuration.

As shown in FIG. 1, the patient 2 wears the external unit 4 on his/her belt, for example, and swallows the capsule endoscope 3.

Then, the capsule endoscope 3 sequentially passes through the esophagus, the stomach, the duodenum, the small intestine and so on. FIG. 5A shows the capsule endoscope 3 is just before the colon 46, and FIG. 5B shows the state that the capsule endoscope 3 reaches the colon 46. Under this state, the capsule endoscope 3 drives the pH sensor 22 through the sensor drive circuit 29 intermittently to detect the pH and sends the result to the control/processing circuit 25. The control/processing circuit 25 determines whether or not the capsule endoscope 3 reaches the colon 46 based on the change in characteristic of the detected pH.

More specifically, since there are digestive juices having a strong acid within the stomach, the pH is 1.0 to 3.5 when the capsule endoscope 3 reaches the stomach. The capsule endoscope 3 passes through the stomach to the duodenum. When digested staffs having the strong acid is sent from the stomach to the duodenum, the digestive juices is neutralized with the strong alkaline digestive juice or bile in the duodenum to neutral (a little lower than pH 7). Then acidity becomes gradually higher by the bacteria in the small intestine (pH is lowered).

Then, the capsule endoscope 3 reaches the colon 46, as shown in FIG. 5B. The higher number of types and the larger amount of bacteria exist in the colon 46 than those in the small intestine. Thus, the acidity is maintained by the lactobacillus bifidus, lactic acid, and so on. As a result, the value of acidity is about pH 6.

As described above, according to this embodiment, when the capsule endoscope 3 enters the stomach, the pH sensor 22 detects the strong acidity under pH 3. Then, when the capsule endoscope 3 enters the duodenum, the pH is increased rapidly under the influence of the strong alkaline digestive juices. After a while, the pH is settled on about pH 7. After that, as the capsule endoscope 3 passes through the small intestine, the pH is decreased gradually (pH 6.5 to 7). When the capsule endoscope 3 enters the colon 46, a little more rapid pH decrease (pH 6.5 to 7) than the gradual pH decrease while moving in the small intestine is detected since the degree of acidity in the colon 46 is higher than that in the small intestine (decrease to about pH 6). Based on the detection of the pH change, it is determined that the capsule endoscope 3 reaches the colon 46.

When the control/processing circuit 25 determines that the capsule endoscope 3 reaches the colon 46, the control/processing circuit 25 sends a signal indicating that the capsule endoscope 3 reaches the target part from the antenna 21 to the outside through the send/receive circuit 28.

When the external unit 4 receives the signal, the control circuit 35 notifies it to the patient 2 and/or medical staffs by turning the lamp 32 on and off. Then, as shown in FIG. 5C, an external ultrasonic wave generator 38 is pressed against the body surface of the patient 2, as shown in FIG. 5C. Then, ultrasonic waves are irradiated toward the capsule endoscope 3.

The microcapsules 14 accommodated in the mesh member 13 of the capsule endoscope 3 are destroyed by the irradiation of the ultrasonic waves. As a result, the forming agent inside is discharged.

The forming agent reacts on the water in the colon 46 and is vaporized, and a large amount of gas is generated. The gas expands the colon 46 as shown in FIG. 5D.

When the fact that the capsule endoscope 3 reaches the colon 46 is detected, the patient 2 lays down so that the capsule endoscope 3 can move forward easily. In this case, the control/processing circuit 25 of the capsule endoscope 3 also controls to operate the LED drive circuit 24 and the CMOS driver 26 intermittently. Thus, image data imaged by the CMOS imager 17 is sent front the antenna 21 to the external unit 4 side by radio waves.

In this case, since the inside of the colon 46 is expanded by the forming agent, the enough visual field of the objective lens 16 can be provided. Thus, the surrounding internal wall can be imaged sufficiently. As a result, the wider wall surface of the colon 46 can be imaged by the CMOS imager 17 (if the colon 46 is not expanded, the transparent member 12 of the objective lens 16 is blocked by the canal wall, for example, of the colon 46. Thus, only a part of the canal wall may not be within the visual field.

The external unit 4 receives image data, which is sent intermittently, and stores the received image data in the memory 34. After the capsule endoscope 3 is excreted from the anus, the external unit 4 is attached to the external unit attaching portion 5. Then, the image data stored in the memory 34 is captured to the display system 7 side.

The operator causes the display device 6 to display the captured image data so that the colon 46 of the patient 2 can be diagnosed.

According to this embodiment, since the capsule endoscope 3 images the subject part, which is expanded, the wider part of the subject can be within the visual field for imaging than that in the case without expansion. As a result, the efficient endoscope examination can be performed. Also, because of the expansion, the surface of the subject is stretched to a substantial plane and is imaged, which helps the diagnosis.

Since the imaging is performed in the part to be examined, the electric energy can be used more efficiently. The operator causes the intermittently imaged image data to display, and the diagnosis can be performed within a shorter period of time.

As a first variation example, a sensor for detecting bacteria, an enzyme or the other, which only exists in the subject (the colon 46 in this embodiment) may be adopted instead of the pH sensor 22.

Figure 6:
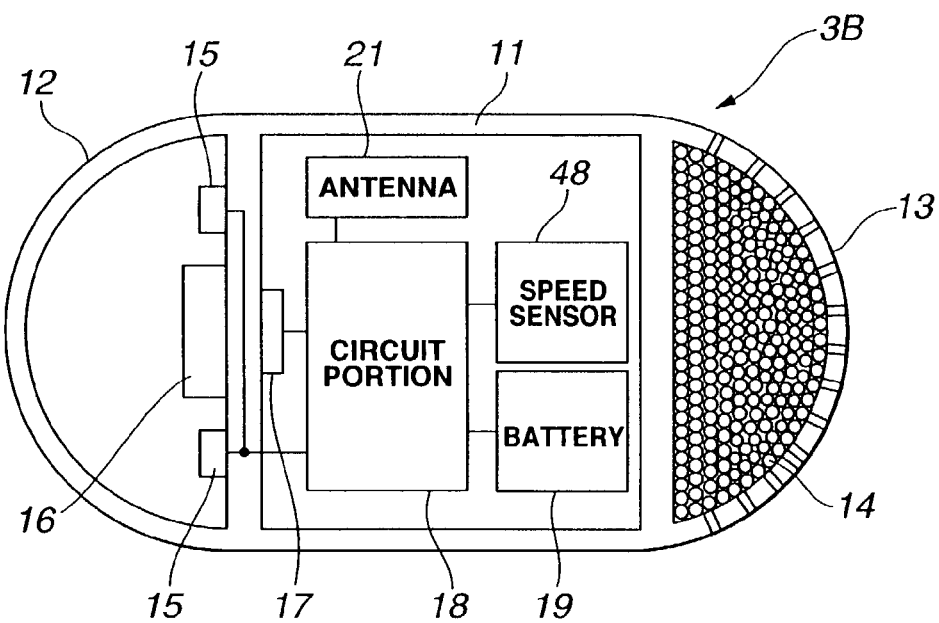

As a second variation example, a speed sensor, for example, may be adopted as a measure for detecting the direction of gravity, instead of the pH sensor 22. FIG. 6 shows a capsule endoscope 3B in the second variation example.

The capsule endoscope 3B adopts a speed sensor 48 instead of the pH sensor 22 in the capsule endoscope 3 in FIG. 3. The speed sensor 48 is connected to the circuit portion 18.

Figure 7:
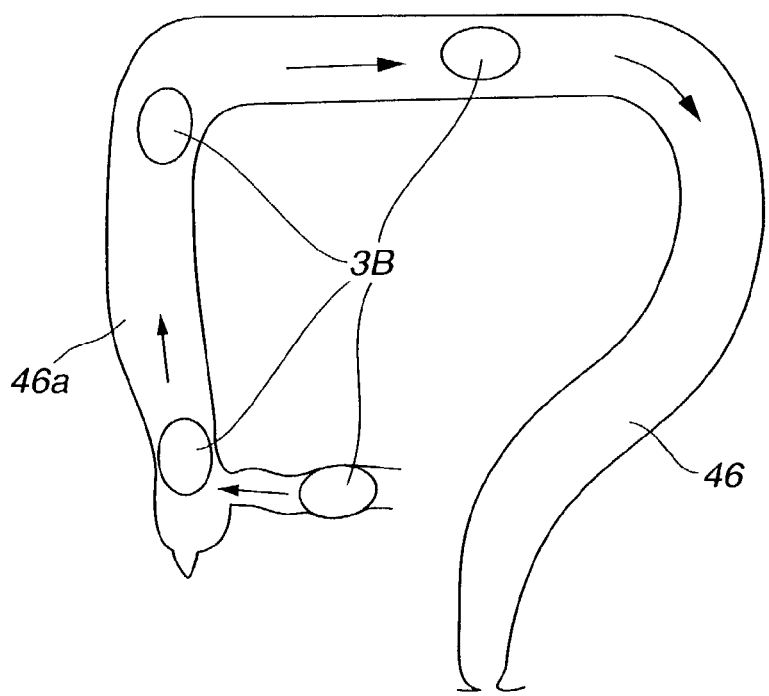

The speed sensor 48 is a sensor for detecting a speed of the capsule endoscope 3B. In this variation example, when the capsule endoscope 3B moves forward from the small intestine to the upstream colon 46a of the colon 46 as shown in FIG. 7, the moving direction is opposite to the gravity direction. Thus, the moving speed of the capsule endoscope 3B becomes extremely low. By detecting the extremely low speed, the fact that the capsule endoscope 3B reaches the colon 46 can be detected.

After the detection, as described in FIG. 5C, the external ultrasonic waves generator 38 is pressed against the body surface of the patient 2 and the ultrasonic waves are irradiated toward the capsule endoscope 3B side. Thus, the microcapsules 14 are destroyed, and the forming agent therein expands the colon 46 so that the imaging can be performed in the visual field obtained in that way.

An acceleration sensor may be adopted instead of the speed sensor 48. In this case, when the capsule endoscope 3B moves from the small intestine to the upstream colon 46a of the colon 46, the fact that the capsule endoscope 3B reaches the target part can be also determined by detecting a large change in the acceleration caused when the capsule endoscope 3B goes to the upward direction.

Advantages of these variation examples are the same as those of the first embodiment.

Second Embodiment

Figure 8A:
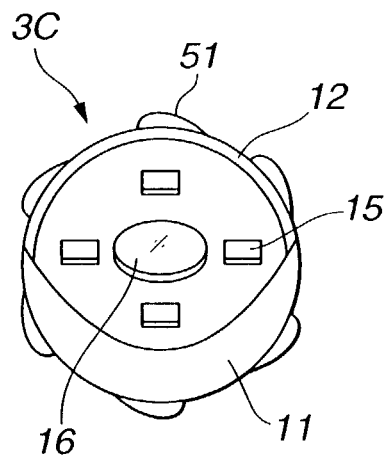
Figure 8B:
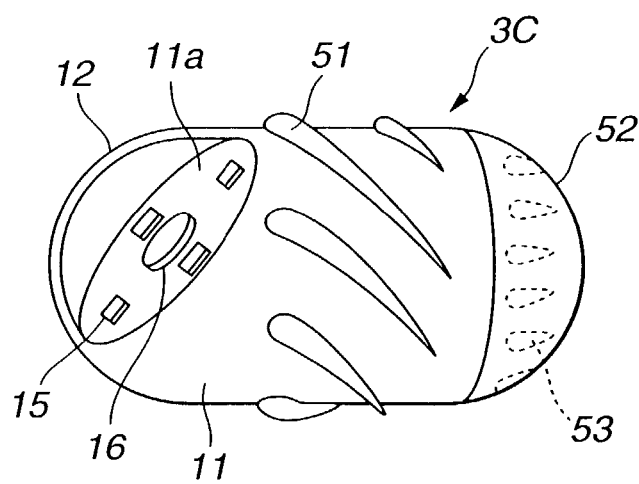
Figure 8C:
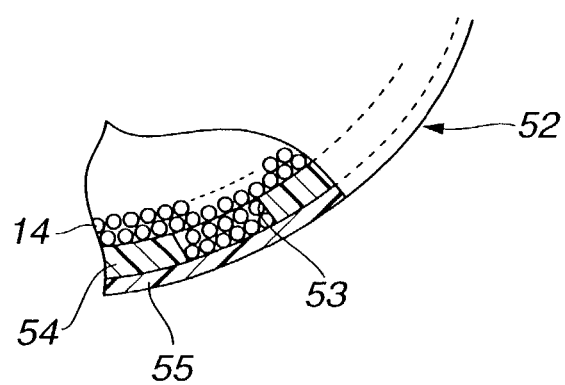
FIG. 8C is a magnified sectional diagram showing a configuration of a microcapsule accommodating portion.

A second embodiment of the present invention will be described with reference to FIGS. 8A to 13. FIGS. 8A and 8B show a capsule endoscope 3C according to the second embodiment of the present invention. FIG. 8A shows a front view of the capsule endoscope 3C, which is viewed from the front side. FIG. 8B shows a perspective view of the capsule endoscope 3C, which is viewed from the substantial side. FIG. 8C shows the internal construction of a microcapsule accommodating portion.

While the capsule endoscope 3 shown in FIGS. 2 and 3 has the illuminating and imaging units in the axis direction, the capsule endoscope 3C shown in FIGS. 8A and 8B has them in the perspective direction, which is slanted with respect to the axis direction.

In other words, the front end side of a cylinder capsule frame body 11 is cut diagonally. Then, a capsule frame body 11 is attached to an objective lens 16 at the center of the part closed by a place frame (base) 11a. The LED's 15 for illumination are located at surrounding four positions, for example. The circumference is covered by a transparent member 12.

Figure 10:
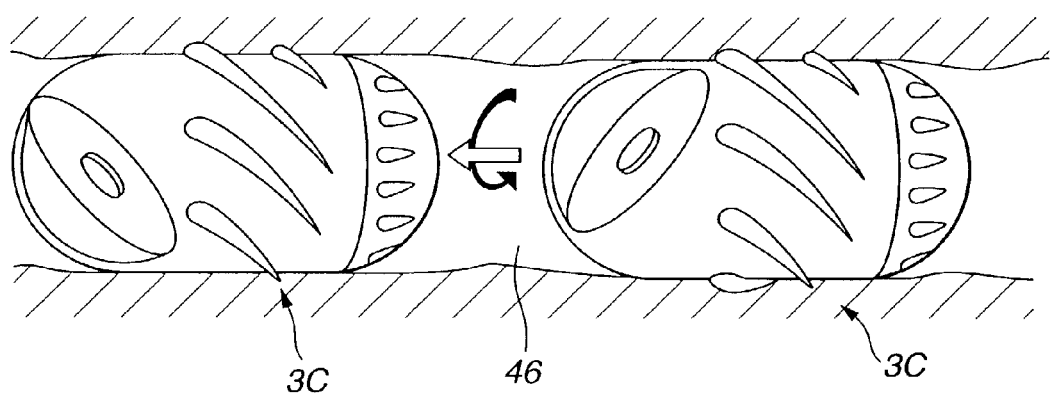

Spiral projections 51 are provided on the peripheral surface of the capsule frame body 11, which allows the capsule endoscope 3C to move forward spirally within the body cavity, as shown in FIG. 10.

The capsule endoscope 3C accommodates the microcapsules 14 in a hemisphere microcapsule accommodating portion 52, which is located at the rear end of the capsule endoscope 3C. In this case, the microcapsule accommodating portion 52 has microcapsule outlets 53 at multiple points, respectively, in the radial direction for discharging the microcapsules 14, as shown in FIG. 8B.

As shown in FIG. 8C, the microcapsule outlets 53 are provided in an accommodating film 54. The microcapsule outlets 53 are covered by an azo-polymer film 55, for example (While the azo-polymer film 55 is provided to cover all of the circumference of the accommodating film 54. However, it may be provided to cover only a part of the microcapsule outlets 53.

In other words, each of the microcapsule outlets 53 has a larger opening than the size of the microcapsule 14. Thus, the opening is covered by the azo-polymer film 55. The azo-polymer film 55 has a characteristic that it is melted by a specific enzyme generated by bacteria in the colon.

Therefore, when the capsule endoscope 3C reaches the colon, the azo-polymer film 55 is melted by the enzyme. Then, each of the microcapsule outlets 53 becomes open. As a result, microcapsules 14 are discharged from the microcapsule outlets 53 to the inside of the colon.

Figure 9A:
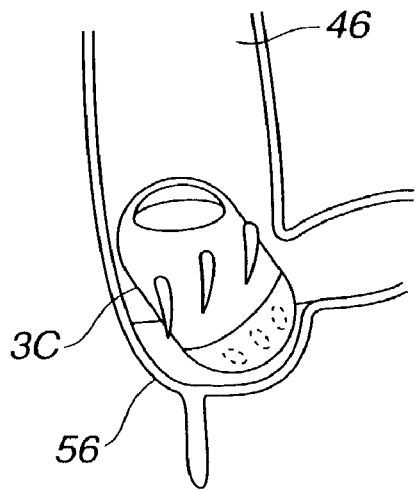
FIGS. 9A to 9D are explanatory diagrams of an operation of this embodiment.
Figure 9B:
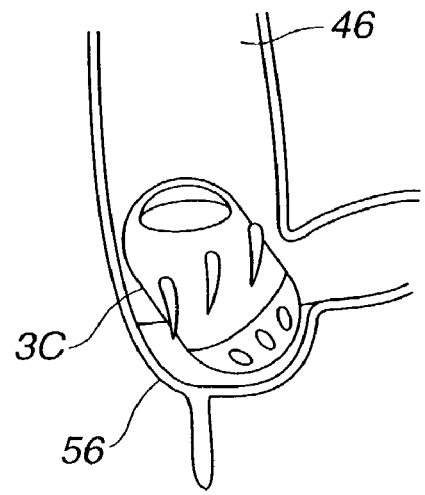

FIGS. 9A to 9D show explanatory diagrams for an operation according to this embodiment. When the capsule-endoscope 3C reaches the appendix 56, for example, of the colon 46, as shown in FIG. 9A, the azo-polymer film 55 on the circumference surface of the microcapsule accommodating portion 52 is melted by the enzyme within the colon 46.

When the azo-polymer film 55 is melted by the enzyme, the microcapsule outlets 53 become open. Then, as shown in FIG. 9C, the microcapsules 14 within the microcapsule accommodating portion 52 are discharged from the microcapsule outlets to the colon 46 side.

Figure 9D:
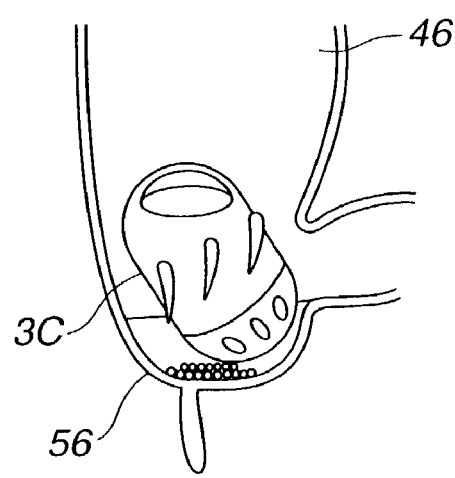
Figure 9C:
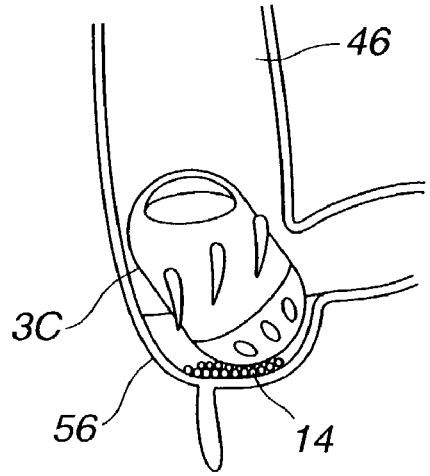

After that, as shown in FIG. 9D, the microcapsules 14 are destroyed (by the irradiation of ultrasonic waves from the outside of the body). The forming agent discharged from the microcapsules 14 is vaporized by water within the colon 46 so that the inside of the colon 46 is expanded. As a result, the visual field can be obtained.

FIG. 10 shows how the capsule endoscope 3C moves forward within the colon 46 when the visual field is obtained by using the forming agent. Since, spiral projections 51 are provided on the circumference surface of the capsule endoscope 3C, the capsule endoscope 3C moves forward by the peristalsis of the colon 46 (the direction of the open arrow in FIG. 10). Additionally, a revolving force works on the capsule endoscope 3C, so that the capsule endoscope 3C revolves and moves forward as indicated by the black arrow. According to the construction, the observation can be performed in the perspective direction. Therefore, the capsule endoscope 3 can move forward with observing (or imaging) the entire canal cavity.

Accordingly, this embodiment has the same advantages as those of the first embodiment. Furthermore, the imaging can be performed through the spiral revolution. Therefore, all of the canal cavity can be imaged easily. Since the perspective-type imaging unit is provided, an image can be obtained, from which the canal cavity can be diagnosed more easily than that in the case of the direct view.

As a first variation example of this embodiment, a forming agent is charged and accommodated within the accommodating film 54 without using the microcapsules 14.

According to the construction of this variation example, the forming agent is vaporized automatically without the irradiation of ultrasonic waves when the capsule endoscope 3C reaches the colon. Thus, the inside of the colon is expanded so that the visual field can be obtained.

Therefore, according to this variation example, the colon can be expanded automatically so that the required operation can be more simplified.

Figure 11:
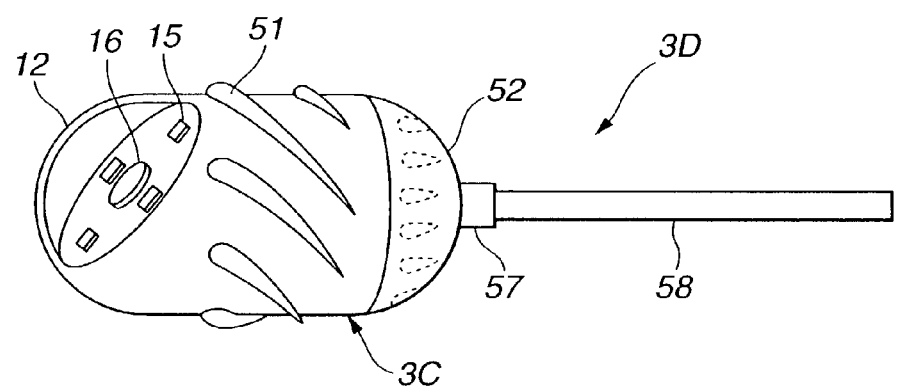

FIG. 11 shows a second variation example. A capsule endoscope 3D is the same as the capsule endoscope 3C in FIG. 8 except the rear end of the capsule endoscope 3D is connected to a cord 58 through a removable joint 57, for example. The connection with the cord 58 can easily set the axis direction of the capsule endoscope 3 to the axis direction of the canal cavity. Furthermore, the unsteadiness of the visual field, which is caused when the capsule endoscope 3D revolves spirally and moves forward, is reduced. Thus, the imaging function to achieve the steady imaging can be improved.

Figure 12A:
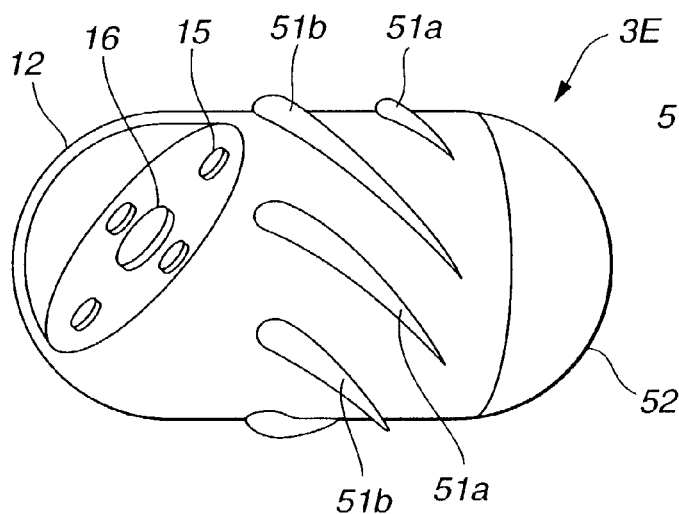
FIGS. 12A and 12B are diagrams showing an appearance and an internal configuration, respectively, of a capsule endoscope in another variation example.
Figure 12B:
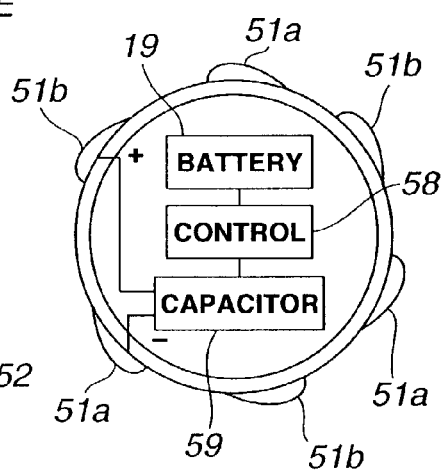
Figure 13:
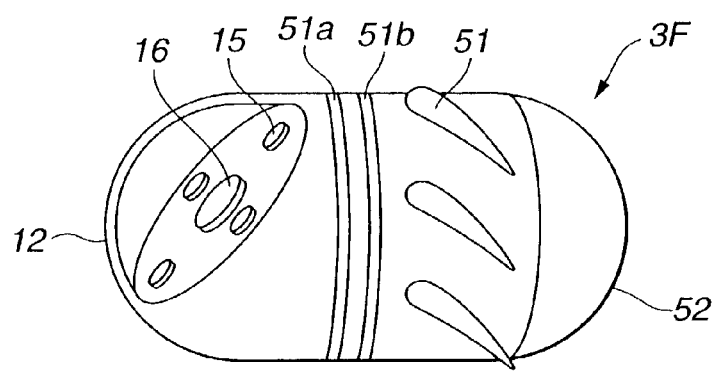

Each of FIGS. 12A and 12B shows a capsule endoscope 3E according to a third variation example. FIG. 12A shows the perspective view. FIG. 12B shows the sectional view showing the principle portion of the internal construction.

The capsule endoscope 3E is the same as the capsule endoscope 3C in FIG. 8 except that functions of bipolar electrodes 51a and 51b to stop bleeding are provided to the projections 51.

In other words, each of the projections 51 are formed by a conductive member to become the bipolar electrodes 51a and 51b. As shown in FIG. 12B, the control circuit 58 is connected to the battery 19, and charges for stopping bleeding are stored in the capacitor 59 by the control circuit 58. After a certain or more of charges are stored, charges in the capacitor 59 are discharged from the bipolar electrodes 51a and 51b, for cauterizing. The LED 15 in this variation example is in a cylinder form, as shown in FIG. 12A.

The functions of the bipolar electrodes 51a and 51b are provided by using projections in FIGS. 12A and 12B. However, in a capsule endoscope 3F shown in FIG. 13, each of the bipolar electrodes 51a and 51b is formed by a ring-shaped conductive member, in addition to the projections 51. By using the capsule endoscope 3E in FIGS. 12A and 12B and the capsule endoscope 3F in FIG. 13, the bleeding can be stopped as well, which improves the functionality.

Third Embodiment

Next, a third embodiment of the present invention will be described with reference to FIGS. 14A to 21. FIG. 14A shows a longitudinal section of a capsule endoscope 3G according to the third embodiment. FIG. 14B shows an exploded view of the capsule endoscope 3G. The capsule endoscope 3G according to this embodiment has a double construction, and the inside portion can be reused.

As shown in FIGS. 14A and 14B, the capsule endoscope 3G has a capsule body 61, a transparent cover 62 for covering the side and the front portions of the capsule body 61, and a back cover 63 for covering a part near the rear end and the rear side part of the capsule body 61.

The capsule body 61 is in a substantial columnar form. An objective lens 16 is mounted at the center of the front end side by using a lens frame. Multiple LED's 15 are located on the peripheral in the circumference direction.

A CMOS imager 17 is located at the focus position of the objective lens 16. A driver 26 therefor is mounted integrally on the back surface. An LED drive circuit 24 for driving the LED's 15 and an antenna 21 are built in the capsule body 61. The driver 26, the LED drive circuit 24 and the antenna 21 are connected with a communication and control circuit 64.

The communication and control circuit 64 has functions of the control/processing circuit 25, the image processing circuit 27 and the send/receive circuit 28 in FIG. 4A.

Electrodes 65a and 65b are mounted on the rear end surface of the capsule body 61. The electrodes 65a and 65b are connected with the communication and control circuit 64. Electrodes 66a and 66b are provided at the positions facing against the electrodes 65a and 65b on the front surface of the back cover 63. When the rear end side of the capsule body 61 is covered by the back cover 63, the electrodes 65a and 66a and the electrodes 65b and 66b contact to each other and are conducted.

Multiple batteries 19 are accommodated in the back cover 63 and are connected to the electrodes 66a and 66b.

A forming agent accommodating portion 68 is formed in a hollow portion near the rear end of the back cover 63 for accommodating a forming agent 67.

Multiple forming agent outlets 69, which communicate with the outside of the back cover 63, are provided at the rear end side of the forming agent accommodating portion 68. The forming agent outlets 69 are covered by an azo-polymer film 70.

In the capsule endoscope 3G having this construction, the capsule body 61 is covered by a transparent cover 62 and the back cover 63. By bonding and fixing the portions fitting the transparent cover 62 and the back cover 63, the capsule body 61 inside can be maintained air-tight and water-tight.

Therefore, after the capsule endoscope 3G is used to perform the endoscope examination on a patient 2, the capsule endoscope 3G is collected and is cleaned and sterilized. After that, the transparent cover 62 and the back cover 63 are removed to take out the capsule body 61.

Then, the capsule body 61 is filled in the new transparent cover 62 and back cover 63 to be used for the next endoscope examination.

According to this embodiment, since the capsule body 61 defining an imaging section and so on can be reused, the cost for the endoscope examination can be reduced significantly.

Figure 15:
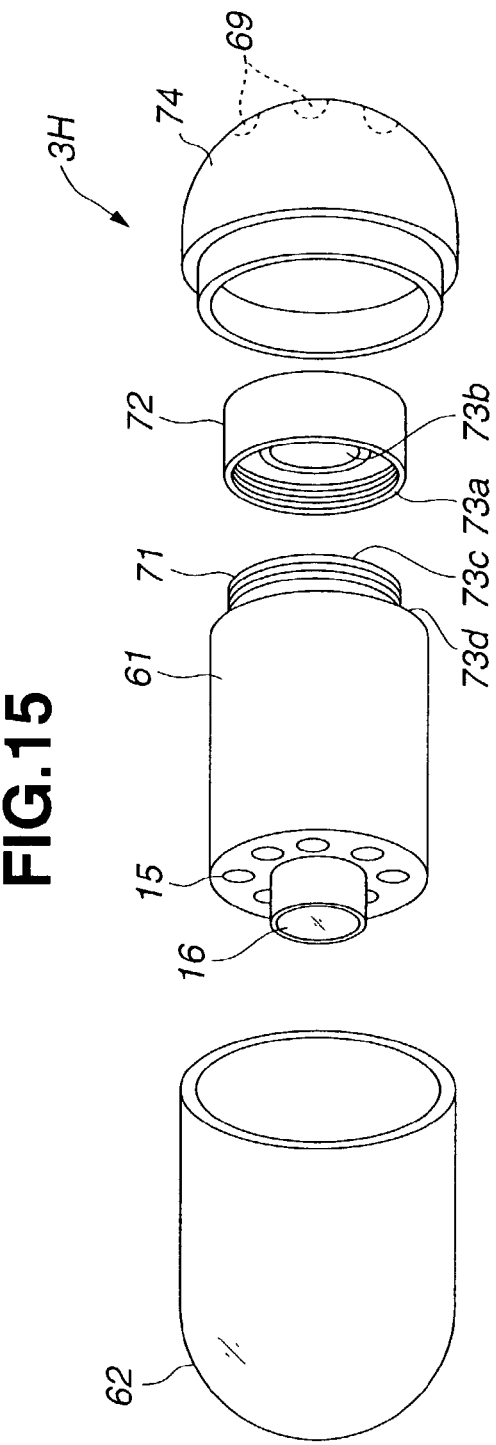

FIG. 15 is an exploded view of a capsule endoscope 3H according to a first variation example of this embodiment. In the case of the capsule endoscope 3H, the batteries 19 within the back cover 63 as shown in FIG. 14A are separated and attached to the rear end of the capsule body 61 removably.

In other words, in this variation example, a screw portion 71 is provided in stepwise on the rear end side of the capsule body 61. Then, a battery box 72 is screwed to the screw portion 71 removably.

The batteries 19, not shown here but shown in FIG. 14A, are accommodated within the battery box 72. In this case, ring-shape electrodes 73c and 73a are provided on the rear end surface of the capsule body 61 and on the front end surface of the battery box 72, respectively (in FIG. 15, the ring shape electrode 73a on the battery box 72 side is conducted with the electrode 73b therein).

When the battery box 72 accommodating batteries 19 is attached to the capsule body 61, the ring-shape electrode 73a on the battery box 72 side is conducted with the step-wise electrode portion 73d on the rear end side of the capsule body 61, which turns on the power supply. After that, like the first embodiment, the capsule body 61 to which the battery box 72 is attached is covered by the transparent cover 62 and a back cover 74 (without batteries 19) air-tightly and water-tightly.

After the capsule endoscope 3H is used for the endoscope examination, it is collected and is cleaned and sterilized. Then, the transparent cover 62 and the back cover 74 are removed to take out the capsule body 61. Then, the battery box 72 is replaced by the new one, and the capsule body 61 is covered by the new transparent cover 62 and back cover 74 to be used for the next endoscope examination.

When the batteries 19 can be still used after the short use, the battery box 72 does not have to be replaced for the next use. In other words, more parts can be reused than those in the case in FIG. 14.

Figure 16:
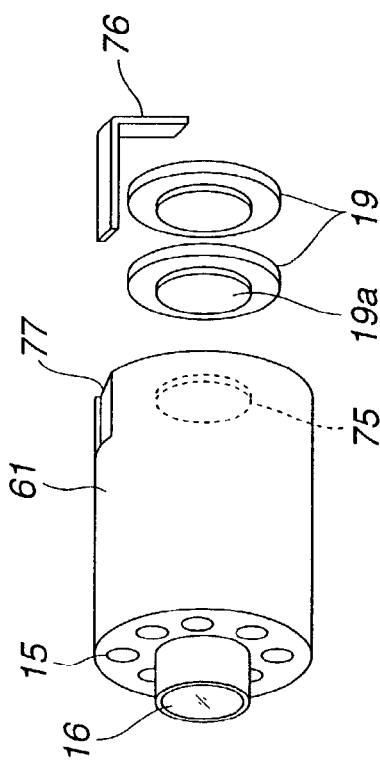

FIG. 16 shows a capsule body and a battery peripheral part in a second variation example. In this variation example, the battery box 72 shown in FIG. 15 is not used. Instead, a depression portion electrode 75, which fits and is conducted with a projection portion electrode 19a of each of the batteries 19, is provided on the rear end surface of the capsule body 61. Additionally, a slot portion electrode 77 is provided, which fits with the front end of and is conducted with the L-shape connecting electrode 76, conducting with the other electrode of each of the batteries 19.

The batteries 19 are electrically connected to the capsule body 61 by using the connection electrode 76, which is then covered by the transparent cover 61 and the back cover 74, like the first variation shown in FIG. 15.

According to the second variation example, there is an advantage that the battery box 72, which is used only once, does not have to be thrown away. Thus, the cost on the parts can be reduced.

Figure 17A:
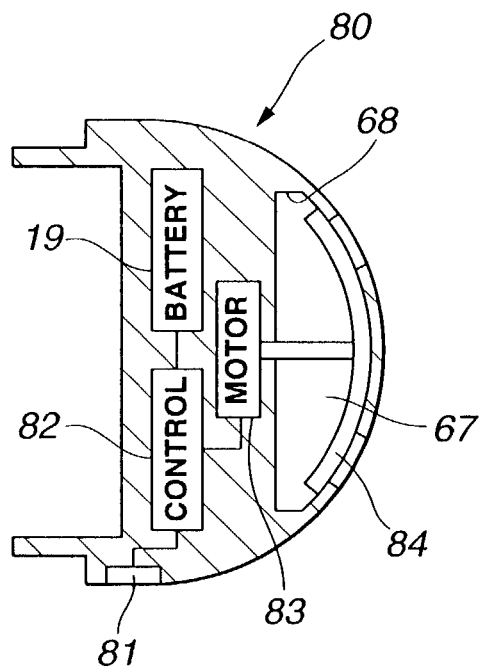
FIGS. 17A and 17B are sectional and back diagrams, respectively, showing a back cover in a third variation example.
Figure 17B:
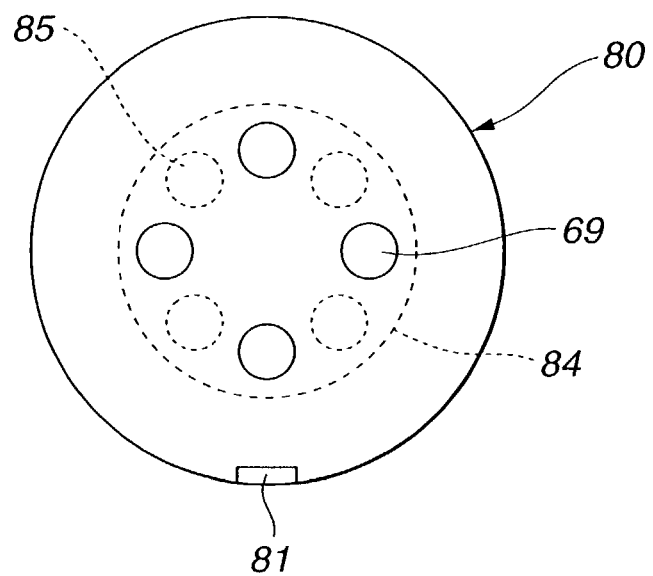

FIGS. 17A and 17B show the construction of a back cover 80 in a third variation example.

The back cover 80 is identical to the back cover 63 of the capsule endoscope 3G in FIG. 14A except that batteries 19, a pH sensor 81, a control circuit 82, a motor 83, and a shutter 84 are mounted on the back cover 80. The pH sensor 81 detects pH. The control circuit 82 detects that the capsule endoscope 3G reaches the colon based on a detection signal from the pH sensor 81. The motor 83 is driven by the control circuit 82 when the capsule endoscope 3G reaches the colon. The pivot of the motor 83 projects to the forming agent accommodating portion 67 side. The shutter 84 is mounted on the end portion so as to contact with the internal wall surface on which the forming agent outlets 69 are provided.

Openings 85 are provided in the shutter 84 as shown in FIG. 17B. The forming agent outlets 69 provided at the rear end of the back cover 80 are closed except for the openings 85 when stopped. When the shutter 84 is rotated by the rotation of the motor 83, and when the forming agent outlets 69 overlaps openings 85 of the shutter 84, the forming agent outlets 69 opens so as to discharge the forming agent 67 for expansion, for example.

In this variation example, the forming agent outlets 69 do not require to be covered by the azo-polymer film 70.

In another variation example, the forming agent outlets 69 are covered by the azo-polymer film 70. A pressure sensor is located in the forming agent accommodating portion 68. Based on a detection signal from the pressure signal, which indicates that the pressure is reduced, the imaging may be started.

In other words, when the forming agent 67 is charged to the forming agent accommodating portion 68, the pressure detected by the pressure sensor indicates a higher value. The azo-polymer film 70 melts when reaching the colon. Then, the forming agent 67 within the forming agent accommodating portion 68 decreases, which reduces the detected pressure. Then, the communication and control circuit 64 in FIG. 14A may start an imaging operation.

Figure 18:
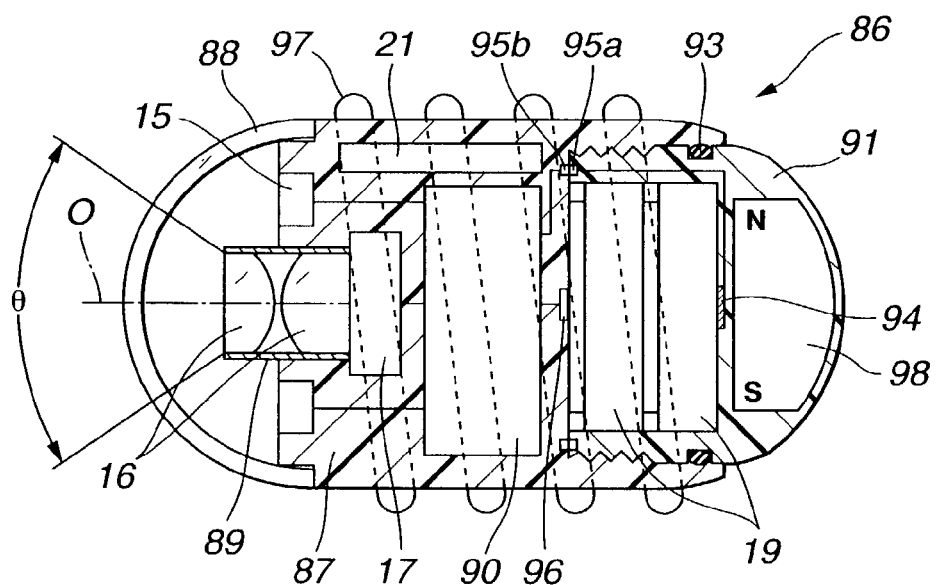

FIG. 18 shows a capsule endoscope 86 according to a fourth variation example.

One of end surface (called pointed end surface, hereinafter) of a capsule body 87 in a substantial columnar form is covered by a transparent cover 88 water-tightly. Then, an imaging unit and an illuminating unit are located at the center part and at the peripheral part of the inside.

More specifically, a lens frame 89 to which an objective lens 16 is mounted is fixed at the center of the pointed end surface of the capsule body 87. A CMOS imager 17, for example, is located at the imaged position. The illuminating unit surrounding the lens frame 89 may be LED's 15, which emits white light, for example.

Then, an observation visual field $\theta$ is formed by using the center axis of the capsule body 87 as an optical axis O of the objective lens 16. The visual field $\theta$ is illuminated by the LED's 15.

The CMOS imager 17 and the LED's 15 are connected to a control circuit 90. The CMOS imager 17 and the LED's 15 are driven under the control of the control circuit 90. The control circuit 90 is connected with an antenna 21 and sends image signals imaged by the CMOS imager 17 to the external unit.

The control circuit 90 is substantially the same as the circuit portion 18 in FIG. 4A except that the control circuit 90 does not have the sensor drive circuit 29.

A depression portion is formed at the rear end surface of the capsule body 87. A battery accommodating portion 91 accommodating batteries 19 is attached to the depression portion removably. The battery accommodating portion 91, which is separate from the capsule body 87, is screwed and attached to the depression portion such that power is supplied to the control circuit 90 of the capsule body 87, which turns on the power supply.

More specifically, a female screw portion is formed on the inner surface of the depression portion. The battery accommodating portion 91 is attached by screwing a male screw portion 92 formed on the peripheral surface of the battery accommodating portion 91 accommodating the batteries 19 into the female screw portion. A peripheral slot is provided at the back of the male screw portion 92 on the peripheral surface of the battery accommodating portion 91. Then, an O-ring 93 for water-tightness is accommodated in the peripheral slot. As shown in FIG. 18, when the battery accommodating portion 91 is attached to the depression portion, the O-ring 93 is pressure-welded to the internal surface of the depression portion such that the inside can be water-tight and no body fluid enters the inside.

A contact 94 is provided in the battery accommodating portion 91 so as to conduct to one of the electrodes of each of the accommodated batteries 19. The contact 94 is connected to a ring-shape contact 95a on the front end surface of the battery accommodating portion 91 through a lead line. The contact 95a is arranged to contact to a ring-shape contact 95b provided on the end surface facing to the capsule body 87 side.

A contact 96 is provided at a position facing to the other electrode of each of the batteries 19 on the capsule body 87 side such that the contact 96 can be slightly projected. The battery accommodating portion 91 is attached to the depression portion so as to conduct to the other electrode of each of the batteries 19. These contacts 95*b* and 96 are connected with the control circuit 90 through a lead line.

Therefore, when the battery accommodating portion 91 is screwed into the depression portion of the capsule body 87, the entire capsule can be water-tight by using the O-ring 93 provided in the battery accommodating portion 91. Thus, the power-supply is turned ON to supply power from the batteries 19 to the control circuit 90 side.

After attaching the battery accommodating portion 91 to the capsule body 87, a rotation stopper, not shown, may be provided for preventing the battery accommodating portion 91 from rotating to be removed (with respect to the capsule body 87).

A spiral-form projections 97 are provided on the peripheral surface of the capsule body 87. The capsule-endoscope 86 is rotated so as to propel the capsule endoscope 86.

According to this embodiment, a permanent magnet 98 is provided in the battery accommodating portion 91, in addition to the batteries 19, which are accommodated replaceably. The permanent magnet 98 is embedded in the battery accommodating 91, for example. The permanent magnet 98 has N and S magnetic poles, which are formed in the direction crossing the center axis of the capsule body 87. Therefore, the magnetic field is applied in the direction crossing the center axis of the capsule body 87. By revolving the magnetic field, the revolving force works on the permanent magnet 98 with the revolution of the magnetic field.

The permanent magnet 98 may be any of a neodymium magnet, a samarium-cobalt magnet, a platinum magnet, and a ferrite magnet, which may be selected in accordance with the required degree of magnetic force.

Figure 19:
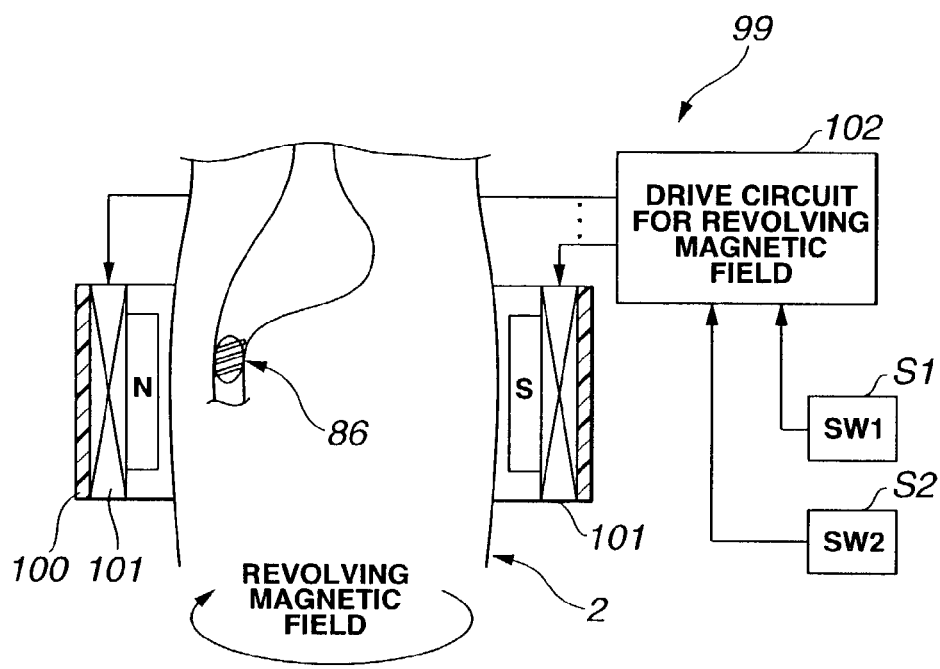

The permanent magnet 98 can apply the revolving magnetic field by using a magnetic field generating device 99 provided at the outside of the body, as shown in FIG. 19.

The magnetic field generating device 99 has multiple electromagnets 101 and a revolving magnetic field drive circuit 102. The multiple electromagnets 101 may be mounted at multiple points, respectively, in the radial direction of a ring-shaped, for example, holding member 100 provided in the outside of the patient 2. The revolving magnetic field drive circuit 102 supplies pulsed drive current to the multiple electromagnets 101 so as to generate the revolving magnetic field.

Then, the patient 2 swallows the capsule endoscope 86. In order to move the capsule endoscope 86 peristaltically and faster from the outside of the body, a switch S1 is turned ON. Thus, pulsed drive current is supplied to a pair of facing electromagnets 101 so as to be magnetized as N and S, respectively. Then, the pulsed drive current is supplied to the next pair of electromagnets 101, which is adjacent to the magnetized pair in the radial direction. In this way, the revolving magnetic field is applied to the abdominal range of the patient 2.

The revolving magnetic field acts to revolve the permanent magnet 98. The revolution of the permanent magnet 98 revolves the capsule endoscope 86 with respect to the axis of the capsule endoscope 86. The spiral-form projection 97 provided on the periphery of the capsule body 87 converts the revolving force of the capsule endoscope 86 to the force propelling the capsule endoscope 86.

In this case, when the spiral-form projection 97 is formed in the right screw form (that is, the capsule endoscope 86 is propelled by revolving the spiral-form projection 97 in clockwise), for example, and when the switch S1 is turned ON, the revolving magnetic field is also generated in clockwise. When a switch S2 is pressed, the revolving magnetic field is generated in counter-clockwise.

Thus, by turning the switch S2 ON and moving the capsule endoscope 86 in the direction opposite to that of the peristalsis, a target part requiring detail observation can be imaged again. Furthermore, by reducing the peristalsis, more images of the target part can be taken.

A cycle adjusting switch S3 is manipulated such that a cycle of the revolving magnetic field can be set variably. Thus, the moving speed can be variably adjusted easily.

Instead of aligning multiple electromagnets 101 in the columnar shape, the revolving magnetic field generating device may be three-axis Helmholtz coil formed by combining three sets of Helmholtz coils diagonally to each other.

According to this variation example, the battery accommodating portion 91, which is separate from the capsule body 87, is attached such that the entire capsule can be water-tight and the power supply can be switched ON. Thus, a switch for turning ON/OFF the power supply is not required, which can simplify the construction of the capsule endoscope 86.

The battery accommodating portion 91 accommodating the batteries 19 is separated from and can be attached to the capsule body 97 removably. The used capsule endoscope 86 can be collected and be cleaned and sterilized or disinfected. Then, the batteries are replaced such that the capsule body 97 and the battery accommodating portion 91 can be reused.

While the batteries 19 may be accommodated removably in the battery accommodating portion 91 in FIG. 18, the batteries 19 may be embedded therein, as shown in FIG. 14A. In this case, the battery accommodating portion 91 requires to be replaced by an unused one for reuse.

Figure 20:
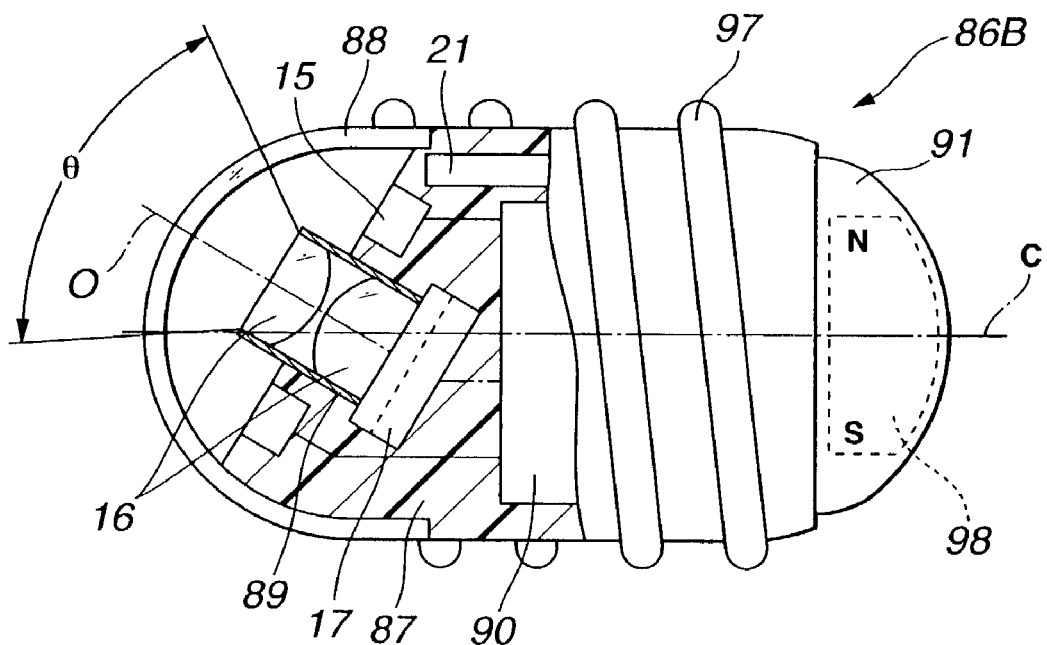

FIG. 20 shows a capsule endoscope 86B in a fifth variation example. The capsule endoscope 86 in FIG. 18 is of the direct-view type having the observation visual field (imaging visual field) where the optical axis O of the objective lens 16 is the fore direction along the center axis, for example, of the capsule body 87. However, the capsule endoscope 86B shown in FIG. 20 is of the perspective type having the observation visual field where the optical axis O of the objective lens 16 is the diagonal, fore direction of the capsule body 87 (that is, the direction slanted with respect to the center axis C, for example, of the capsule body 87).

The other configuration is the same as that in FIG. 18. Therefore, the explanation will be omitted here.

When a patient swallows the capsule endoscope 86B and the capsule endoscope 86B is moved and revolved by the peristalsis within the canal cavity, the same effect is obtained as that in the second embodiment. The visual field is changed continuously so as to observe the wider range. In other words, the observation functionality can be improved.

The revolving magnetic field is generated by the magnetic field generating device 99 provided externally, that is, in the outside of the body, as shown in FIG. 19, such that the direction of the observation visual field of the capsule endoscope 86B may be changed during the revolution.

Figure 21:
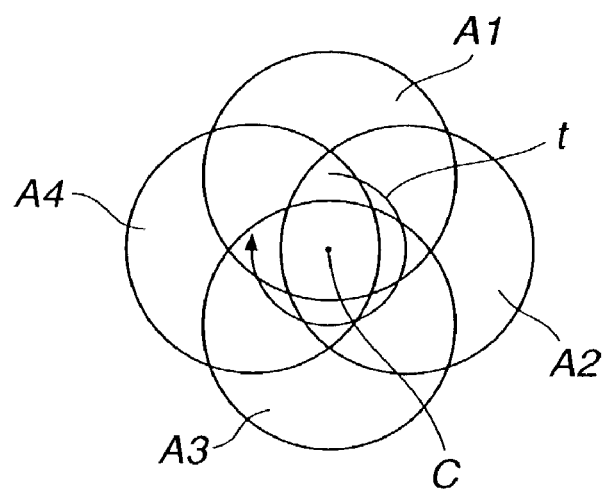

As shown in FIG. 21, an observation visual field range A1 is obtained when the direction of the observation visual field of the capsule endoscope 86B before the revolution directs to the diagonal upper direction, for example. The observation visual field range A1 becomes an observation visual field range A2 by revolving the capsule endoscope 86B by 90°. By revolving the capsule endoscope 86B by 90° and 180°, the observation visual field ranges A3 and A4 can be obtained, respectively.

In this case, the center of the observation visual field range $A_i$ draws a locus t, which is similar to a circle around the center axis C of the capsule endoscope 86B. When the revolution is caused by the revolving magnetic field from the outside of the body in this way, the imaging range may be adjusted by increasing the revolution speed, for example.

In other words, the range to be observed through the revolution, as shown in FIG. 21, can be still wider even when the magnetic field is not applied from the outside of the body. However, the revolution speed cannot be adjusted. On the other hand, when the revolution magnetic field is applied from the outside of the body, the revolution speed can be adjusted freely. Thus, places to be imaged can be adjusted not to overlap each other even when the imaging cycle is constant.

Movement control may be used such that the capsule endoscope can reach the subject part fast by revolving faster and propelling the capsule endoscope.

According to the fifth variation example, the wider range of the canal cavity can be observed like the second embodiment. In addition, the capsule endoscope can be revolved by the application of the magnetic field from the outside of the body. The revolution speed in this case may be adjusted to perform imaging properly. Furthermore, the advancing speed may be changed.

According to the above-described embodiments, the imaged image data is sent from the capsule endoscope 3, for example, to the external unit 4, for example, by RF signals such as microwaves. The image data may be sent to the outside of the body by magnetic signals, for example.

An embodiment arranged by combining the above-described embodiments partially belongs to the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule-type medical apparatus, comprising:
   an imaging device for imaging and an illuminating device for illumination,
   cylindrical body for containing the imaging device and illuminating device, the cylindrical body having a spiral projection formed on an exterior of the cylindrical body, and
   a magnet in the cylindrical body, the magnet being magnetized in one predetermined direction perpendicular to a cylinder axis of the cylindrical body,
   wherein by an application of a revolving magnetic field generated from a magnetic field generating device arranged external to a patient's body into which the capsule-type medical apparatus is inserted, the entirety of the magnet, which is placed in the cylindrical body and magnetized only in one predetermined direction perpendicular to the cylinder axis, generates a rotating force which rotates the cylindrical body with a rotation axis thereof in a longitudinal direction of the cylindrical body in such a manner as to follow rotation of the revolving magnetic field;
   the rotating force serves as a propelling force to move the capsule-type medical apparatus in one or the other direction in the longitudinal direction of the cylindrical body depending on a spiral direction of the spiral projection; and
   the imaging device and the illuminating device are provided in the direction of a cylinder axis of the exterior.

2. A capsule-type medical apparatus according to claim 1, wherein the magnet is removably attached.

3. A capsule-type medical apparatus according to claim 1, wherein at least part of the spiral-form portion is made of a conductive member to work as an electrode.

4. A capsule-type medical apparatus according to claim 1, further comprising a forming agent.

5. A capsule-type medical apparatus according to claim 1, further comprising a switch for selectively setting a magnetic field generated by a magnetic field generating device to one of clockwise and anticlockwise directions.

6. A capsule-type medical apparatus, comprising:
   an imaging device for imaging and an illuminating device for illumination,
   cylindrical body for containing the imaging device and illuminating device, the cylindrical body having a spiral projection formed on an exterior of the cylindrical body, and
   a magnet in the cylindrical body, the magnet being magnetized in one predetermined direction perpendicular to a cylinder axis of the cylindrical body,
   wherein by an application of a revolving magnetic field generated from a magnetic field generating device arranged external to a patient's body into which the capsule-type medical apparatus is inserted, the entirety of the magnet, which is placed in the cylindrical body and magnetized only in one predetermined direction perpendicular to the cylinder axis, generates a rotating force which rotates the cylindrical body with a rotation axis thereof in a longitudinal direction of the cylindrical body in such a manner as to follow rotation of the revolving magnetic field;
   the rotating force serves as a propelling force to move the capsule-type medical apparatus in one or the other direction in the longitudinal direction of the cylindrical body depending on a spiral direction of the spiral projection; and
   the imaging device and the illuminating device are provided in the diagonal direction with respect to a cylinder axis of the exterior.

7. A capsule-type medical apparatus according to claim 6, wherein the magnet is removably attached.

8. A capsule-type medical apparatus according to claim 6, wherein at least part of the spiral-form portion is made of a conductive member to work as an electrode.

9. A capsule-type medical apparatus according to claim 6, further comprising a forming agent.

10. A capsule-type medical apparatus according to claim 6, further comprising a switch for selectively setting a magnetic field generated by a magnetic field generating device to one of clockwise and anticlockwise directions.

11. A method for operating a capsule-type medical apparatus located in a body cavity, the method comprising:
    locating in the body cavity a capsule-type medical apparatus having a spiral projection formed on an exterior of a cylindrical body and a magnet, the magnet being magnetized in one predetermined direction perpendicular to a cylinder axis of the cylindrical body;
    applying a revolving external magnetic field generated from a magnetic field generating device arranged external to a patient's body into which the capsule-type medical apparatus is inserted,
    applying the revolving magnetic field on the entirety of the magnet which is placed in the cylindrical body and magnetized only in one predetermined direction perpendicular to the cylinder axis, thereby generating a rotating force which rotates the cylindrical body with a rotation axis thereof in a longitudinal direction of the cylindrical body in such a manner that the entirety of the magnet follows rotation of the revolving magnetic field;

moving by the rotating force the capsule-type medical apparatus in one or the other direction in the longitudinal direction of the cylindrical body depending on a spiral direction of the spiral projection; and controlling a progress of the capsule-type medical apparatus based on a control of the revolving magnetic field.

12. A method according to claim 11, further comprising selecting a direction of a revolving magnetic field generated by the external magnetic field, to allow selection between movements in one and the other directions in the longitudinal direction of the capsule-type medical apparatus.

13. A method for performing processing for examination within a body cavity, the method comprising:

introducing a capsule-type medical apparatus having an imaging device into a body cavity;

imaging within the body cavity to perform the examination;

rotating the capsule-type medical apparatus with a rotation axis thereof in a longitudinal direction of the cylindrical body to change the imaging direction by the imaging device, the imaging device having an imaging direction in a predetermined direction which is different from a longitudinal direction of a cylindrical body that forms an exterior, and having an observation visual field range which is set to include the longitudinal direction of the cylindrical body; and repeating the imaging and the rotating of the capsule-type medical apparatus.

14. A method according to claim 13, further comprising applying a magnetic field for rotating the capsule-type medical apparatus from the outside of the body prior to the rotating of the capsule-type medical apparatus.

15. A method according to claim 13, further comprising propelling the capsule-type medical apparatus.

16. A method for performing processing for examination within a body cavity, the method comprising:

introducing a capsule-type medical apparatus having an imaging device and a cylindrical body into a body cavity, the cylindrical body having a spiral projection formed on a cylindrical peripheral surface and a magnet which is magnetized only in one predetermined direction perpendicular to a cylinder axis;

imaging within the body cavity to perform the examination;

applying a revolving magnetic field generated from a magnetic field generating device arranged external to a patient's body into which the capsule-type medical apparatus is inserted, thereby propelling the capsule-type medical apparatus in a predetermined direction along a cylinder axis depending on a spiral direction of the spiral projection; and performing a switch operation to reverse the direction of the revolving magnetic field when it is desired to move the capsule-type medical apparatus in a direction opposite to the predetermined direction.

17. A method according to claim 16, further comprising operating to change a revolving direction of the magnetic field for revolving the capsule-type medical apparatus while the capsule-type medical apparatus is revolved and propelled, to enable it to move from one direction to the other direction in the longitudinal direction of the capsule-type medical apparatus.

* * * * *